US011022658B2

(12) United States Patent
Ledbetter et al.

(10) Patent No.: US 11,022,658 B2
(45) Date of Patent: Jun. 1, 2021

(54) NEURAL FEEDBACK LOOP FILTERS FOR ENHANCED DYNAMIC RANGE MAGNETOENCEPHALOGRAPHY (MEG) SYSTEMS AND METHODS

(71) Applicant: HI LLC, Los Angeles, CA (US)

(72) Inventors: Micah Ledbetter, Sunnyvale, CA (US); Ricardo Jiménez-Martinez, Culver City, CA (US); Ethan Pratt, Santa Clara, CA (US); Hooman Mohseni, Wilmette, IL (US); Jamu Alford, Lake Arrowhead, CA (US)

(73) Assignee: HI LLC

( * ) Notice: Subject to any disclaimer, the term of this patent is extended or adjusted under 35 U.S.C. 154(b) by 0 days.

(21) Appl. No.: 16/752,393

(22) Filed: Jan. 24, 2020

(65) Prior Publication Data
US 2020/0256929 A1    Aug. 13, 2020

Related U.S. Application Data

(60) Provisional application No. 62/837,574, filed on Apr. 23, 2019, provisional application No. 62/804,539, filed on Feb. 12, 2019.

(51) Int. Cl.
*G01R 33/032* (2006.01)
*G01R 33/028* (2006.01)
(Continued)

(52) U.S. Cl.
CPC ......... *G01R 33/032* (2013.01); *G01N 24/006* (2013.01); *G01R 33/0041* (2013.01);
(Continued)

(58) Field of Classification Search
CPC .. G01R 33/032; G01R 33/028; G01R 33/326; G01R 33/26; G01R 33/282;
(Continued)

(56) References Cited

U.S. PATENT DOCUMENTS 3,173,082 A  *  3/1965  Bell ..................... G01R 33/26
                                                  324/304
3,257,608 A  *  6/1966  Bell ..................... G01R 33/26
                                                  324/304
(Continued)

FOREIGN PATENT DOCUMENTS

CN        10730484       6/2015
CN        107562188      1/2018
(Continued)

OTHER PUBLICATIONS

Tierney, T.M., Holmes, N., Meyer, S.S., Boto, E., Roberts, G., Leggett, J., . . . Barnes, G. R. (2018). Cognitive neuroscience using wearable magnetometer arrays: Non-invasive assessment of language function. NeuroImage, 181, 513-520.
(Continued)

*Primary Examiner* — Jay Patidar
(74) *Attorney, Agent, or Firm* — Branch Partners PLLC; Bruce E. Black

(57) ABSTRACT

One embodiment is a magnetic field measurement system that includes at least one magnetometer having a vapor cell, a light source to direct light through the vapor cell, and a detector to receive light directed through the vapor cell; at least one magnetic field generator disposed adjacent the vapor cell; and a feedback circuit coupled to the at least one magnetic field generator and the detector of the at least one magnetometer. The feedback circuit includes at least one feedback loop that includes a first low pass filter with a first cutoff frequency. The feedback circuit is configured to compensate for magnetic field variations having a frequency lower than the first cutoff frequency. The first low pass filter rejects magnetic field variations having a frequency higher than the first cutoff frequency and provides the rejected
(Continued)

magnetic field variations for measurement as an output of the feedback circuit.

20 Claims, 3 Drawing Sheets

(51) Int. Cl.
   *G01R 33/32* (2006.01)
   *G01N 24/00* (2006.01)
   *G01R 33/025* (2006.01)
   *G01R 33/00* (2006.01)

(52) U.S. Cl.
   CPC .......... *G01R 33/025* (2013.01); *G01R 33/028* (2013.01); *G01R 33/326* (2013.01)

(58) Field of Classification Search
   CPC ............ G01R 33/0041; G01R 33/0094; G01R 33/025; A61B 5/245; G01N 24/006
   USPC .................................. 324/304–305
   See application file for complete search history.

(56) References Cited

U.S. PATENT DOCUMENTS

| | | | |
|---|---|---|---|
| 3,495,161 A * | 2/1970 | Bell ........................ | G04F 5/14 324/304 |
| 3,501,689 A * | 3/1970 | Robbiano .............. | G01R 33/26 324/304 |
| 3,513,381 A * | 5/1970 | Happer, Jr. ............ | G01R 33/26 324/304 |
| 4,193,029 A * | 3/1980 | Cioccio .................. | G01R 33/26 324/301 |
| 4,951,674 A | 8/1990 | Zanakis et al. | |
| 5,189,368 A | 2/1993 | Chase | |
| 5,192,921 A | 3/1993 | Chantry et al. | |
| 5,225,778 A * | 7/1993 | Chaillout ............... | G01R 33/26 324/304 |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A | 8/1995 | Wikswo, Jr. et al. | |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 6,144,872 A | 11/2000 | Graetz | |
| 6,339,328 B1 | 1/2002 | Keene et al. | |
| 6,472,869 B1 | 10/2002 | Upschulte et al. | |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 * | 5/2006 | Romalis ................. | G01R 33/02 324/301 |
| 7,102,451 B2 | 9/2006 | Happer et al. | |
| 7,145,333 B2 | 12/2006 | Romalis et al. | |
| 7,521,928 B2 | 4/2009 | Romalis et al. | |
| 7,656,154 B2 | 2/2010 | Kawabata et al. | |
| 7,826,065 B1 | 11/2010 | Okandan et al. | |
| 7,872,473 B2 | 1/2011 | Kitching et al. | |
| 7,994,783 B2 | 8/2011 | Ledbetter et al. | |
| 8,054,074 B2 | 11/2011 | Ishihara et al. | |
| 8,212,556 B1 | 7/2012 | Schwindt et al. | |
| 8,258,884 B2 | 9/2012 | Borwick, III et al. | |
| 8,319,156 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |
| 8,587,304 B2 | 11/2013 | Budker et al. | |
| 8,836,327 B2 | 9/2014 | French et al. | |
| 8,906,470 B2 | 12/2014 | Overstolz et al. | |
| 8,941,377 B2 | 1/2015 | Mizutani et al. | |
| 9,084,549 B2 | 7/2015 | Desain et al. | |
| 9,095,266 B1 | 8/2015 | Fu | |
| 9,116,201 B2 | 8/2015 | Shah et al. | |
| 9,140,590 B2 | 9/2015 | Waters et al. | |
| 9,140,657 B2 | 9/2015 | Ledbetter et al. | |
| 9,169,974 B2 | 10/2015 | Parsa et al. | |
| 9,244,137 B2 | 1/2016 | Kobayashi et al. | |
| 9,291,508 B1 | 3/2016 | Biedermann et al. | |
| 9,343,447 B2 | 5/2016 | Parsa et al. | |
| 9,366,735 B2 | 6/2016 | Kawabata et al. | |
| 9,383,419 B2 | 7/2016 | Mizutani et al. | |
| 9,395,425 B2 | 7/2016 | Diamond et al. | |
| 9,417,293 B2 | 8/2016 | Schaffer et al. | |
| 9,568,565 B2 | 2/2017 | Parsa et al. | |
| 9,575,144 B2 | 2/2017 | Kornack et al. | |
| 9,601,225 B2 | 3/2017 | Parsa et al. | |
| 9,638,768 B2 | 5/2017 | Foley et al. | |
| 9,639,062 B2 | 5/2017 | Dyer et al. | |
| 9,677,905 B2 | 6/2017 | Waters et al. | |
| 9,726,626 B2 | 8/2017 | Smith et al. | |
| 9,726,733 B2 | 8/2017 | Smith et al. | |
| 9,791,536 B1 | 10/2017 | Alem et al. | |
| 9,829,544 B2 | 11/2017 | Bulatowicz | |
| 9,846,054 B2 | 12/2017 | Waters et al. | |
| 9,851,418 B2 | 12/2017 | Wolf et al. | |
| 9,869,731 B1 | 1/2018 | Hovde et al. | |
| 9,915,711 B2 | 3/2018 | Kornack et al. | |
| 9,927,501 B2 | 3/2018 | Kim et al. | |
| 9,948,314 B2 | 4/2018 | Dyer et al. | |
| 9,964,609 B2 | 5/2018 | Ichihara et al. | |
| 9,964,610 B2 | 5/2018 | Shah et al. | |
| 9,970,999 B2 | 5/2018 | Larsen et al. | |
| 9,995,800 B1 | 6/2018 | Schwindt et al. | |
| 10,024,929 B2 | 7/2018 | Parsa et al. | |
| 10,088,535 B1 | 10/2018 | Shah | |
| 10,162,016 B2 | 12/2018 | Gabrys et al. | |
| 10,194,865 B2 | 2/2019 | Le et al. | |
| 10,314,508 B2 | 6/2019 | Desain et al. | |
| 10,371,764 B2 * | 8/2019 | Morales ................. | G01R 33/26 |
| 2004/0232912 A1 | 11/2004 | Tsukamoto et al. | |
| 2005/0007118 A1 | 1/2005 | Kitching et al. | |
| 2005/0046851 A1 | 3/2005 | Riley, Jr. et al. | |
| 2005/0206377 A1 | 9/2005 | Romalis et al. | |
| 2007/0076776 A1 | 4/2007 | Lust et al. | |
| 2007/0120563 A1 | 5/2007 | Kawabata et al. | |
| 2007/0167723 A1 | 7/2007 | Park et al. | |
| 2007/0205767 A1 | 9/2007 | Xu et al. | |
| 2009/0079426 A1 | 3/2009 | Anderson | |
| 2009/0101806 A1 | 4/2009 | Masuda | |
| 2010/0219820 A1 | 9/2010 | Skidmore et al. | |
| 2011/0062956 A1 | 3/2011 | Edelstein et al. | |
| 2012/0112749 A1 | 5/2012 | Budker et al. | |
| 2013/0082700 A1 | 4/2013 | Mizutani et al. | |
| 2013/0082701 A1 | 4/2013 | Mizutani et al. | |
| 2013/0265042 A1 | 10/2013 | Kawabata et al. | |
| 2014/0121491 A1 | 5/2014 | Zhang | |
| 2014/0306700 A1 | 10/2014 | Kamada et al. | |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0219732 A1 * | 8/2015 | Diamond ............. | A61B 5/0522 324/201 |
| 2015/0378316 A1 | 12/2015 | Parsa et al. | |
| 2016/0061913 A1 | 3/2016 | Kobayashi et al. | |
| 2016/0116553 A1 * | 4/2016 | Kim ..................... | G01R 33/032 324/305 |
| 2016/0223627 A1 | 8/2016 | Shah et al. | |
| 2016/0291099 A1 | 10/2016 | Ueno | |
| 2016/0313417 A1 | 10/2016 | Kawabata et al. | |
| 2017/0023653 A1 | 1/2017 | Kobayashi et al. | |
| 2017/0023654 A1 | 1/2017 | Kobayashi et al. | |
| 2017/0067969 A1 * | 3/2017 | Butters ................. | G01R 33/26 |
| 2017/0199138 A1 | 7/2017 | Parsa et al. | |
| 2017/0199251 A1 | 7/2017 | Fujii et al. | |
| 2017/0261564 A1 | 9/2017 | Gabrys et al. | |
| 2017/0331485 A1 | 11/2017 | Gobet et al. | |
| 2017/0343617 A1 | 11/2017 | Manickam et al. | |
| 2017/0343695 A1 | 11/2017 | Stetson et al. | |
| 2017/0356969 A1 | 12/2017 | Ueno | |
| 2018/0003777 A1 | 1/2018 | Sorensen et al. | |
| 2018/0038921 A1 | 2/2018 | Parsa et al. | |

(56) References Cited

U.S. PATENT DOCUMENTS

| | | |
|---|---|---|
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2019/0391213 A1 | 12/2019 | Alford |
| 2020/0025844 A1 | 1/2020 | Alford et al. |
| 2020/0057115 A1 | 2/2020 | Jiménez-Martínez et al. |
| 2020/0057116 A1 | 2/2020 | Zorzos et al. |
| 2020/0072916 A1 | 3/2020 | Alford et al. |
| 2020/0088811 A1 | 3/2020 | Mohseni |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |

OTHER PUBLICATIONS

Boto, E, Holmes, N, Leggett, J, Roberts, G, Shah, V, Meyer, SS, Munoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

International Search Report and Written Opinion for PCT/US2020/015055 dated May 15, 2020.

Allred, J.C., Lyman, R. N., Kornack, T. W., & Romalis, M. V. (2002). Hight-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Talenczuk, B., Paul, E., . . . & Ouanounou, G. (2016), Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoenephalography," Opt. Express 24, 15403-15416 (2016).

Dang, H.B. & Maloof, A.C. & Romalis, Michael. (2009). Ultra-high sensitivity magnetic field and magnetization measurement with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a mircrofabricated Cs vapor cell. Physical Review Applied (10).ISSN 2331-7019.

Jiménez-Martinez, R., Griffith, W. C., Wang, Y. J., Knappe, S., Kitching, J., Smith, K., & Prouty, M. D. (2010). Sensitivity comparison of Mx and frequency-modulated bell—bloom Cs magnetometers in a microfabricated cell. IEEE Transactions on Instruments and Measurement, 59(2), 372-378.

Kiwoong Kim, Samo Begus, Hui Xia, Seung-Kyun Lee, Vojko Jazbinsek, Zconko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG Magnetoencephalography: From Signals to Dynamics Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp,631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84, 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett. 110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10. 1063/1.3056152.

(56) References Cited

OTHER PUBLICATIONS

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-017-20352-x.

Kim, Young Jin & Savukov, I. (2016). Ultra-sensitiive Magnetic Microscopy with an Optically Pumped Magnetometer. Scientifiic Reports. 6. 24773. 10.1038/srep24773.

Navau, Caries & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69) 90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62 .23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

Larry J, Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 78(12), 4 pages.

F. Jackson Kimball, D & Dudley, J & Li, Y & Thulasi, Swencha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-933355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US vol. 13, No. 1, Jan. 1, 2013 (Jan. 1, 2013), pp. 186-189.

Arjen Stolk, Ana Todorovic, Jan-Mathijs Schoffelen, and Robert Oostenveld. "Online and offline tools for head movement compensation in MEG." Neuroimage 68 (2013): 39-48.

Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi:10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.

J. M. Leger et. al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space , 53 (10), 949-958.

Boma, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Jusitalo M and Ilmoniemi R., 1997, Signal-space projection method for separating MEG or EEG into components. Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

(56) References Cited

OTHER PUBLICATIONS

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jiménez-Martínez R, Kennedy DJ, Rosenbluh M. et al. Optical hyperpolarization and NMR detection of 129Xe on a microfluidic chip. Nat Commun. 2014;5:3908. Published May 20, 2014. doi:10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel Squid Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.
Pasquarelli, A, M De Melis, Laura Marzetti, Hans-Peter Müller, and S N Emé. "Calibration of a Vector-MEG Helmet System." Neurology & Clinical Neurophysiology□: NCN 2004 (Feb. 1, 2004): 94.
Pfeiffer, Christoph, Lau M. Andersen, Daniel Lundqvist, Matti Hämäläinen, Justin F. Schneiderman, and Robert Oostenveld. "Localizing On-Scalp MEH Sensors Using an Array of Magnetic Dipole Coils." PLOS ONE 13, No. 5 (May 10, 2018): e0191111.
Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.
Nagel, S., & Spüler, M. (2019). Asynchronous non-invasive high-speed BCI speller with robust non-control state detection. Scientific Reports, 9(1), 8269.
Thielen, J., van den Broek, P., Farquhar, J., & Desain, P. (2015). Broad-Band Visually Evoked Potentials: Re(con)volution in Brain-Computer Interfacing. PloS One, 10(7), e0133797. https://doi.org/10.1371/journal.pone.0133797.
J. Kitching, "Chip-scale atomic devices," Appl. Phys. Rev. 5(3), 031302 (2018), 39 pages.
Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

\* cited by examiner

NEURAL FEEDBACK LOOP FILTERS FOR ENHANCED DYNAMIC RANGE MAGNETOENCEPHALOGRAPHY (MEG) SYSTEMS AND METHODS

CROSS-REFERENCE TO RELATED APPLICATIONS

This application claims the benefit of U.S. Provisional Patent Application Ser. No. 62/804,539, filed Feb. 12, 2019, and 62/837,574, filed Apr. 23, 2019, both of which are incorporated herein by reference in their entireties.

FIELD

The present disclosure is directed to the area of magnetic field measurement systems using one or more optically pumped magnetometers. The present disclosure is also directed to magnetic field measurement systems and methods that include a feedback loop filter to facilitate detection or measurement of low amplitude magnetic fields.

BACKGROUND

In the nervous system, neurons propagate signals via action potentials. These are brief electric currents which flow down the length of a neuron causing chemical transmitters to be released at a synapse. The time-varying electrical currents within an ensemble of neurons generates a magnetic field, which can be measured using either a Superconductive Quantum Interference Device (SQUID) or an Optically Pumped Magnetometer (OPM). In this disclosure the OPM is primarily considered because the SQUID requires cryogenic cooling, which may make it prohibitively costly for users and too large to be wearable by a user. Magnetoencephalography (MEG), the measurement of magnetic fields generated by the brain, is one application of interest.

BRIEF SUMMARY

One embodiment is a magnetic field measurement system that includes at least one magnetometer having a vapor cell, a light source to direct light through the vapor cell, and a detector to receive light directed through the vapor cell; at least one magnetic field generator disposed adjacent the vapor cell and configured to modify a magnetic field experienced by the vapor cell; and a feedback circuit coupled to the at least one magnetic field generator and the detector of the at least one magnetometer. The feedback circuit includes at least one feedback loop and each of the at least one feedback loop includes a first low pass filter with a first cutoff frequency. The feedback circuit is configured to compensate for magnetic field variations having a frequency lower than the first cutoff frequency using the at least one magnetic field generator. The first low pass filter rejects magnetic field variations having a frequency higher than the first cutoff frequency. The feedback circuit is configured to provide the rejected magnetic field variations for measurement as an output of the feedback circuit.

In at least some embodiments, the first cutoff frequency is in a range of 5 to 40 Hz. In at least some embodiments, the first cutoff frequency is in a range of 8 to 20 Hz.

In at least some embodiments, each of the at least one feedback loop of the feedback circuit includes a proportional integral derivative (PID) element. In at least some embodiments, the first low pass filter is part of the PID element.

In at least some embodiments, at least one of the at least one feedback loop of the feedback circuit further includes a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit. In at least some embodiments, at least one of the at least one feedback loop of the feedback circuit further includes a modulation source configured to provide modulation at a modulation frequency to a feedback signal generated by the feedback circuit and delivered to the magnetic field generator, wherein the modulation frequency is greater than the second cutoff frequency.

In at least some embodiments, the feedback circuit includes two of the feedback loops. In at least some embodiments, the magnetic field generator includes two pairs of coils, wherein each of the pairs is arranged orthogonal to the other pair and is coupled to one of the two feedback loops.

In at least some embodiments, the feedback circuit includes three of the feedback loops. In at least some embodiments, the magnetometer further includes a pump light source configured to illuminate and pump atoms in the vapor cell. In at least some embodiments, the magnetic field generator includes three pairs of coils, wherein each of the pairs is arranged orthogonal to the other pairs and is coupled to one of the three feedback loops. In at least some embodiments, two of the three feedback loops of the feedback circuit further include a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit. In at least some embodiments, two of the three feedback loops of the feedback circuit further include a modulation source configured to provide modulation at a modulation frequency to a feedback signal generated by the feedback circuit and delivered to the magnetic field generator, wherein the modulation frequency is greater than the second cutoff frequency.

Another embodiment is a magnetic field measurement system that includes an array of magnetometers, each of the magnetometers including a vapor cell, a light source to direct light through the vapor cell, and a detector to receive light directed through the vapor cell, wherein the array of magnetometers includes a first magnetometer; at least one magnetic field generator, wherein the vapor cell of each of the magnetometers is disposed adjacent at least one of the at least one magnetic field generator which is configured to modify a magnetic field experienced by the vapor cell; and a feedback circuit coupled to each of the at least one magnetic field generator and the detector of the first magnetometer. The feedback circuit includes at least one feedback loop and each of the at least one feedback loop includes a first low pass filter with a first cutoff frequency. The feedback circuit is configured to compensate, in each of the magnetometers, for magnetic field variations having a frequency lower than the first cutoff frequency using the at least one magnetic field generator. The first low pass filter rejects magnetic field variations having a frequency higher than the first cutoff frequency. The feedback circuit is configured to provide the rejected magnetic field variations for measurement as an output of the feedback circuit.

In at least some embodiments, each of the at least one feedback loop of the feedback circuit includes a proportional integral derivative (PID) element. In at least some embodiments, the first low pass filter is part of the PID element.

In at least some embodiments, at least one of the at least one feedback loop of the feedback circuit further includes a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit.

In at least some embodiments, the feedback circuit includes two of the feedback loops. In at least some embodiments, the feedback circuit includes three of the feedback loops.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
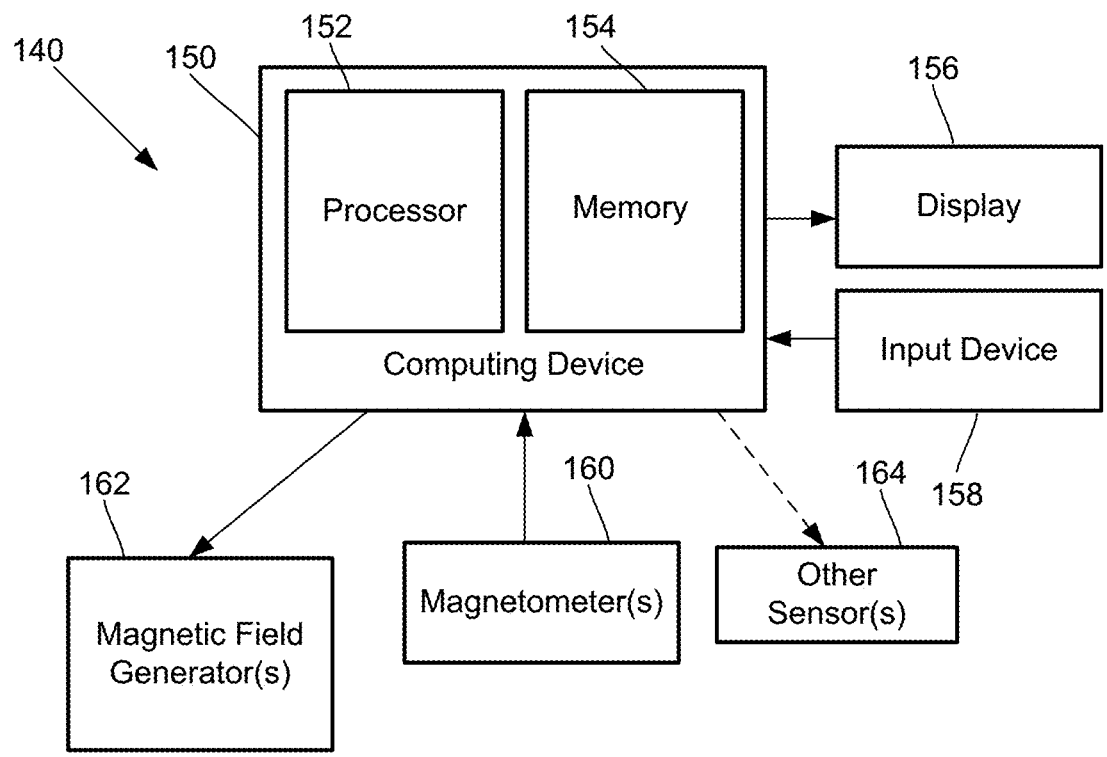
FIG. 1A is a schematic block diagram of one embodiment of a magnetic field measurement system, according to the invention.

The present disclosure is directed to the area of magnetic field measurement systems using one or more optically pumped magnetometers. The present disclosure is also directed to magnetic field measurement systems and methods that include a feedback loop filter to facilitate detection or measurement of low amplitude magnetic fields.

Herein the terms "ambient background magnetic field" and "background magnetic field" are interchangeable and used to identify the magnetic field or fields associated with sources other than the magnetic field measurement system and the biological source(s) (for example, neural signals from a user's brain) or other source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more sources (for example, neural signals or other biological sources). The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be used outside a magnetically shielded room.

FIG. 1A is a block diagram of components of one embodiment of a magnetic field measurement system 140. The system 140 can include a computing device 150 or any other similar device that includes a processor 152 and a memory 154, a display 156, an input device 158, one or more magnetometers 160 (for example, an array of magnetometers) which can be OPMs, one or more magnetic field generators 162, and, optionally, one or more sensors 164. The system 140 and its use and operation will be described herein with respect to the measurement of neural signals arising from signal sources in the brain of a user as an example. It will be understood, however, that the system can be adapted and used to measure other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions, as described below.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangement can also be used. The optional sensor(s) 164 can include, but are not limited to, one or more magnetic field sensors, position sensors, orientation sensors, accelerometers, image recorders, or the like or any combination thereof.

The one or more magnetometers 160 can be any suitable magnetometer including, but not limited to, any suitable optically pumped magnetometer. In at least some embodiments, at least one of the one or more magnetometers (or all of the magnetometers) of the system is arranged for operation in the SERF mode. Examples of magnetic field measurement systems or methods of making such systems or components for such systems are described in U.S. patent application Ser. Nos. 16/213,980; 16/405,382; 16/418,478; 16/418,500; 16/428,871; 16/456,975; 16/457,655; 16/573,394; 16/573,524; 16/679,048; and 16/741,593, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; and 62/960,548, all of which are incorporated herein by reference in their entireties.

Figure 1B:
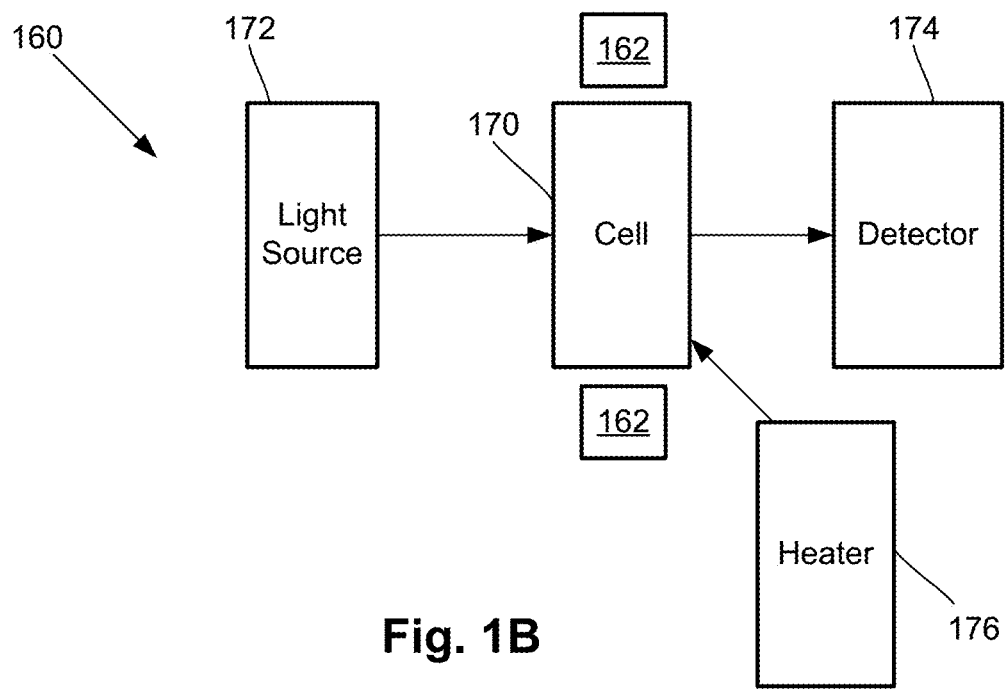
FIG. 1B is a schematic block diagram of one embodiment of a magnetometer, according to the invention.

FIG. 1B is a schematic block diagram of one embodiment of a magnetometer 160 which includes an alkali metal gas cell 170 (also referred to as a "cell" or "vapor cell"); a heating device 176 to heat the cell 170; a light source 172; and a detector 174. In addition, coils of a magnetic field generator 162 can be positioned around the vapor cell 170. The gas cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and to probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
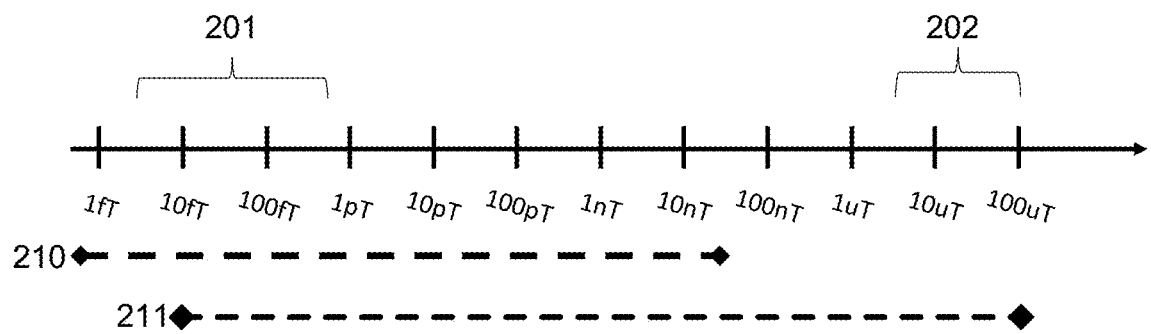
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 µT.

FIG. 2 also illustrates a challenge in measuring neural and other biological signals; namely the measurement of signals with a dynamic range of, for example, approximately $5 \times 10^9$ which corresponds to the ratio of the amplitude of a neural signal (approximately 10 fT) to the amplitude of the Earth's magnetic field (approximately 50 µT). Conventionally, MEG signals have been recorded by SQUIDs or optically pumped magnetometers (OPMs) inside large, immobile, and expensive magnetically shielded rooms. The magnetic shield isolates the subject from the Earth's magnetic field of around 50 µT and suppresses a variety of environmental sources of noise. The magnetic shield also reduces the dynamic range used to measure small neural signals which are in the range of 10-100 fT. In the case of OPMs, spin-exchange relaxation-free (SERF) magnetometers that feature a narrow resonance (from 0 to 10-100 nT) centered on zero magnetic field have been used to demonstrate MEG. Outside of this range the atoms in the OPM lose sensitivity to magnetic fields.

These shielded rooms, however, are generally not viable for a consumer market where it is thought that magnetic field measurements systems for MEG should be able to operate in the ambient background magnetic field of the native environment, including the Earth's magnetic field and other local sources of magnetic fields. One additional conventional solution is to incorporate a feedback system to null magnetic fields at the OPM magnetometer operating in the SERF mode. In this arrangement, the current in the feedback coils becomes a measure of the magnetic field. This enables the SERF magnetometer to operate in finite magnetic fields, however it does not address the issue of measuring signals with a dynamic range of $5 \times 10^9$.

In contrast to these conventional arrangements, a new arrangement circumvents the need for such high dynamic range by incorporating a low-pass filter into a feedback loop. Most environmental magnetic field noise and noise due to subject motion occurs at low frequencies (below approximately 10 Hz) and neural signals often occur at higher frequencies (above approximately 50 Hz). The ability of a feedback loop with a low pass filter to track low frequency fluctuations thus reduces the needed dynamic range in the frequency band of interest as the higher amplitude magnetic fields are filtered out due to their low frequency fluctuations. Furthermore, at least some embodiments of the present arrangements can incorporate the same OPM for zero-field finding which may reduce system cost and simplify its use.

In at least some embodiments, the arrangements described herein can enhance the dynamic range of optically pumped magnetometers (OPMs) in magnetic field measurements systems for magnetoencephalography (MEG) to facilitate applications, systems, and arrangements for use outside of magnetically shielded rooms. In at least some embodiments, an arrangement, device, or system as described herein can separate high-frequency neural signals (for example, above a pre-selected or user-defined cutoff frequency) from low frequency noise (in the band from continuous to the pre-selected or user-defined cutoff frequency) arising due to, for example, external field perturbations or user motion in an ambient background magnetic field.

The arrangements and their use and operation will be described herein with respect to the measurement of neural signals arising from signal sources in the brain of a user as an example. It will be understood, however, that these arrangements can be adapted and used to measure other neural signals, other biological signals, or other non-biological signals.

Figure 3:
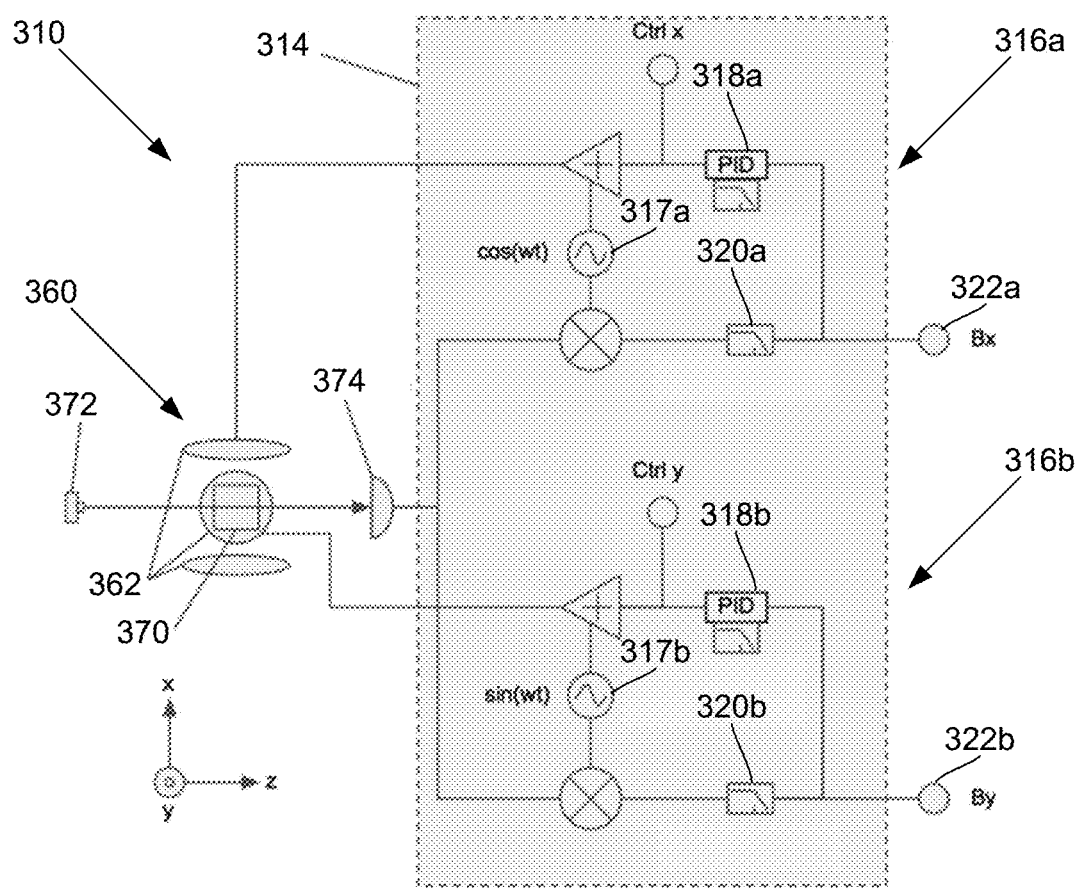
FIG. 3 is a schematic view of one embodiment of an arrangement of magnetometer and a demodulation and feedback circuit, according to the invention.

FIG. 3 illustrates one embodiment of an OPM arrangement 310 where two feedback loops are employed to reduce or zero the magnetic field in two directions based on a signal obtained from a single beam transmission mode magnetometer 360. In FIG. 3, the arrangement includes an optically pumped magnetometer 360 operating in closed loop mode to enable detection of weak, high-frequency neural signals on top of a much larger, slowly varying ambient background magnetic field. A light source 372, such as a laser, optically pumps a vapor cell 370. Laser light transmitted through the vapor cell 370 is monitored via a detector 374, such as a photodiode. A magnetic field generator 362 (for example, a set of feedback coils) is used to generate small magnetic field modulations (for example, 10 nT amplitude at 1 kHz) and to compensate for external magnetic field fluctuations. For example, the magnetic field generator 362 can include one set of feedback coils to compensate for magnetic field fluctuations in the x-direction and one set of feedback coils to compensate for the magnetic field fluctuations in the y-direction.

A demodulation and feedback circuit 314 receives the signal from the detector 374 and uses that signal for purposes including, but not limited to, 1) generation of the small magnetic field modulation using the magnetic field generator 362 to convert the vapor cell absorptive resonance (with respect to the magnetic field) into a dispersively shaped error signal in the first harmonic of the demodulated signal, and 2) to implement a feedback loop that can compensate for slowly varying ambient background magnetic field perturbations by running the appropriate quasi-static current through the magnetic field generator 362 to generate a magnetic field near the vapor cell 370.

The demodulation and feedback circuit 314 in FIG. 3 includes two feedback loops 316a, 316b for two directions (orthogonal directions "x" and "y" in the illustrated embodiment but any other suitable directions can be used.) Each feedback loop 316a, 316b includes a modulation source 317a, 317b. In at least some embodiments, the modulation frequency is higher than the estimated frequency of the signals to be detected such as neural signals. In at least some embodiments, the modulation frequency is at or above, for example, 100, 200, 250, 500, 1000 Hz or higher.

Each feedback loop 316a, 316b also includes a first low pass filter 318a, 318b with a cutoff frequency that passes the slow motions of many background ambient magnetic field variations but excludes the higher frequency neural signals. In the embodiment of FIG. 3, the first low pass filter is part of a proportional integral derivative (PID) element. As examples, the cutoff frequency for the low pass filter 318a, 318b of the PID element can be in the range of 5 to 40 Hz or in the range of 8 to 20 Hz or, for example, 5, 8, 10, 12, 15, 20, or 25 Hz. Since the low pass filter 318a, 318b of the PID element only passes low frequency signals to the magnetic field generator 362, high frequency neural signals originating from the brain remain in the demodulated first harmonic signal. Applications for such neural signals include, but are not limited to identification of cognitive processes, interfaces with computers, control of prosthetics, and the like. Examples of non-invasive magnetic field measurement applications systems or methods are described in U.S. patent application Ser. No. 16/364,338 and U.S. Provisional Patent Application Ser. Nos. 62/829,124; 62/894,578; and 62/891,128, all of which are incorporated herein by reference.

Each feedback loop may also include a second low pass filter 320a, 320b with a cutoff frequency higher than the frequency of the neural signals to be detected. This second low pass filter 320a, 320b may remove higher frequency magnetic field variations, as well as interference from the modulation frequency. The cutoff frequency is selected to be higher than the signals to be detected and may be lower than the modulation frequency. For example, the cutoff frequency can be at least 100, 150, 200, 250 Hz, 500 Hz, or more.

An output 322a, 322b between the low pass filter 320a, 320b and low pass filter 318a, 381b of the PID element provides the neural signal. In at least some embodiments, at the output 322a, 322b, the dispersively shaped error signal from the detector 374, as modified by the demodulation and feedback circuit 314, is linear with respect to the neural signals to be detected.

Figure 4:
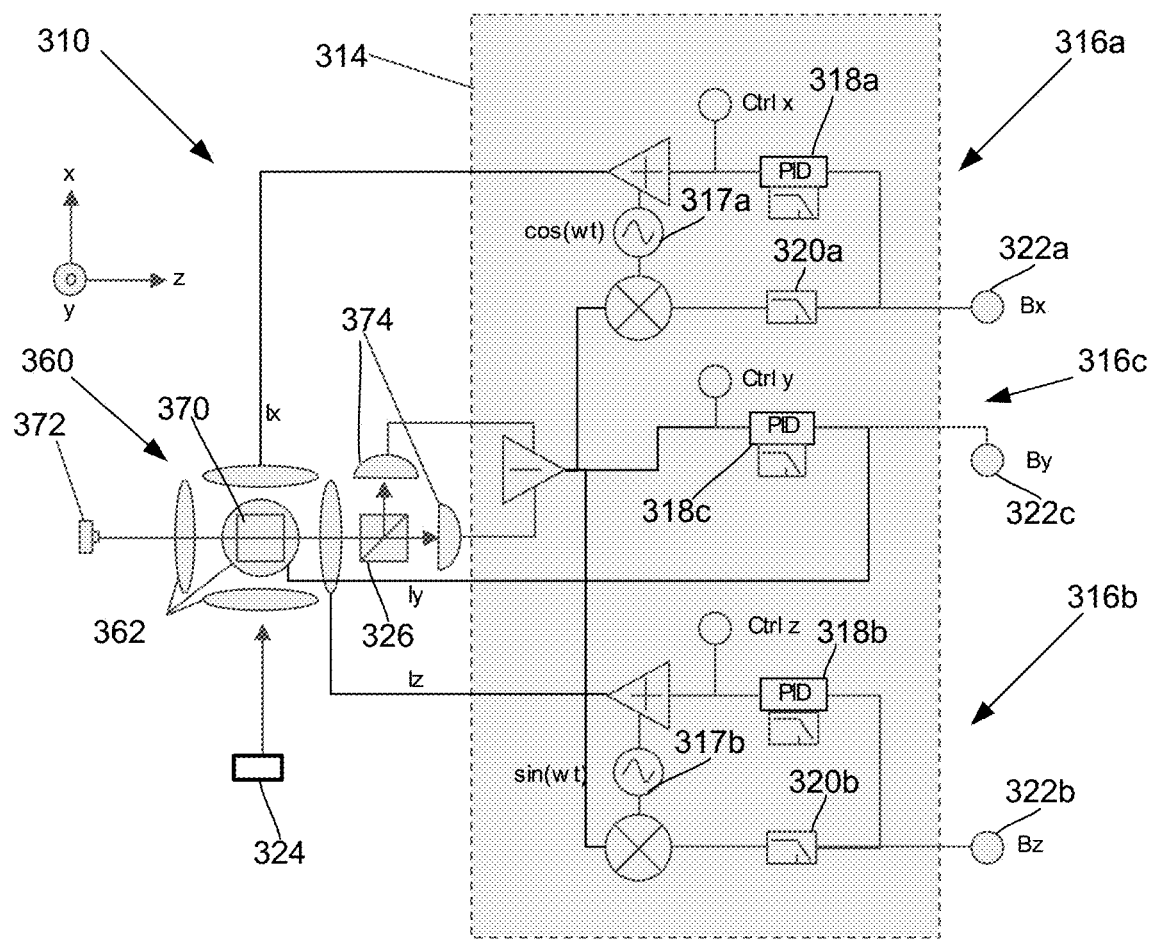
FIG. 4 is a schematic view of another embodiment of an arrangement of magnetometer and a demodulation and feedback circuit, according to the invention.

The arrangement illustrated in FIG. 3 utilizes a transmission mode SERF magnetometer and a single laser beam and is sensitive to only two components of magnetic field. Other embodiments can include two laser beams and are sensitive to three magnetic field components. In at least some of these embodiments, three separate feedback loops can be used. One such embodiment is illustrated in FIG. 4 with three feedback loops 316a, 316b, 316c. This arrangement 310 includes a probe laser 372, a pump laser 324, a vapor cell 370, detectors 374, a polarizing beamsplitter 326, and a magnetic field generator 362 with sets of feedback coils in all three orthogonal axes.

The demodulation and feedback circuit 314 in FIG. 4 includes three feedback loops 316a, 316b, 316c. Two of the feedback loops 316a, 316b includes a modulation source 317a, 317b. Each feedback loop 316a, 316b, 316c also includes a first low pass filter 318a, 318b, 318c with a cutoff frequency that passes the slow motions of many background ambient magnetic field variations but excludes the higher frequency neural signals. In the embodiment of FIG. 4, the first low pass filter is part of a proportional integral derivative (PID) element. As examples, the cutoff frequency for the low pass filter 318a, 318b, 318c of the PID element can be in the range of 5 to 40 Hz or in the range of 8 to 20 Hz or, for example, 5, 8, 10, 12, 15, 20, or 25 Hz.

Two of the feedback loops 316a, 316b may also include a second low pass filter 320a, 320b with a cutoff frequency higher than the frequency of the neural signals to be detected. This low pass filter 320a, 320b may remove higher frequency magnetic field variations, as well as interference from the modulation frequency. The cutoff frequency is selected to be higher than the signals to be detected and may be lower than the modulation frequency. An output 322a, 322b, 322c prior to the low pass filter 318a, 318b, 318c of the PID element provides the neural signal.

Magnetic field measurement systems involving superconducting quantum interference device magnetometers may also benefit from the feedback loop arrangements presented above.

Figure 5:
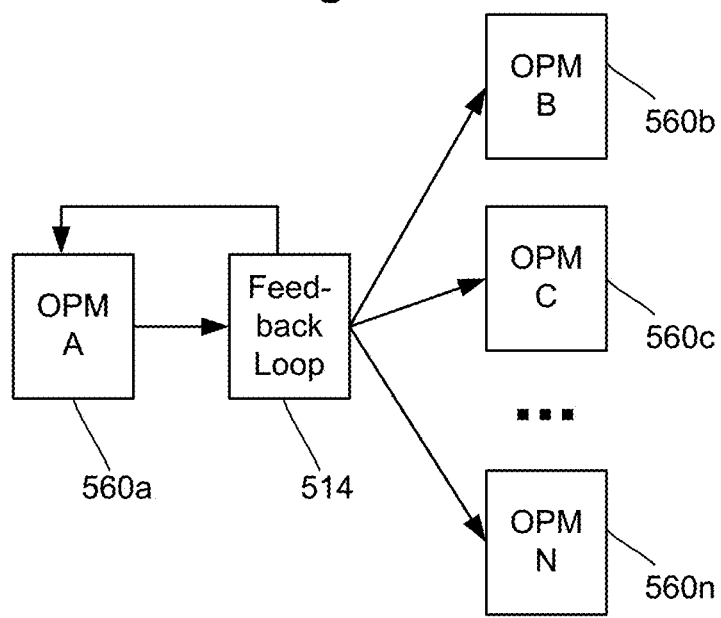
FIG. 5 is a block diagram of one embodiment of an array of magnetometers that operate using control signals from a demodulation and feedback circuit associated with one of the magnetometers, according to the invention.

Another embodiment utilizes more than one magnetometer in an array. FIG. 5 illustrates one embodiment of an array of magnetometers 560a, 560b, 560c, . . . 560n, the control signal from the feedback loop 514 (for example, the signal provided to the magnetic field generator 362 from the feedback loops 316a, 316b in FIG. 3) of the first magnetometer 560a may be used to correct the magnetic field of other OPMs 560b, 560c, . . . 560n in a local array. For example, the control signal from the feedback loop 514 can be provided to magnetic field generators of the magnetometers 560b, 560c, . . . 560n (or a single magnetic field generator for the entire array or magnetic field generators for multiple magnetometers). As examples, either of the arrangements in FIGS. 3 and 4 can be used for the first magnetometer 560a and the feedback loop 514 with the signals directed to the magnetic field generator 362 in FIGS. 3 and 4 also being directed to the other magnetometers 560b, 560c, . . . 560n. In at least some embodiments of this array configuration, the first magnetometer 560a may be different in sensitivity or dynamic range from the other magnetometers or may not be an OPM; for example, the first magnetometer could be a fluxgate or other magnetic field sensing device. In these embodiment, signals from the additional sensors can be used to generate magnetic field gradient information.

In at least some instances, the embodiments presented above can also be placed inside a shield, such as a wearable passively shielded enclosures or a shielded room, to reduce the ambient background magnetic field.

Examples of magnetic field measurement systems in which the embodiments presented above can be incorporated, and which present features that can be incorporated in the embodiments presented herein, are described in U.S. patent application Ser. Nos. 16/213,980; 16/405,382; 16/418,478; 16/418,500; 16/428,871; 16/456,975; 16/457,655; 16/573,394; 16/573,524; 16/679,048; and 16/741,593, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; and 62/960,548, all of which are incorporated herein by reference in their entireties.

In at least some embodiments, a magnetic field measurement system or other system, arrangement, device, or method can incorporate a feedback control loop with a low frequency cut off to correct for user motion/movement without disrupting the recording/detection of neural signals.

In at least some embodiments, the arrangements described herein incorporate a slow feedback loop to suppress low frequency noise in the demodulated magnetometer signal. This enables a SERF magnetometer to operate in finite fields, such as those found outside shielded rooms, which is desirable for commercialization of a wearable device and may reduce the dynamic range to manageable levels for neural signals in a high pass band.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetic field measurement system, comprising:
at least one magnetometer comprising a vapor cell, a light source configured to direct light through the vapor cell, and a detector configured to receive light directed through the vapor cell;
at least one magnetic field generator disposed adjacent the vapor cell and configured to modify a magnetic field experienced by the vapor cell; and
a feedback circuit coupled to the at least one magnetic field generator and the detector of the at least one magnetometer, wherein the feedback circuit comprises at least two feedback loops, wherein each of the at least two feedback loops comprises a first low pass filter with a first cutoff frequency, wherein each of the at least two feedback loops of the feedback circuit is configured to compensate for magnetic field variations having a frequency lower than the first cutoff frequency using the at least one magnetic field generator, wherein the first low pass filter rejects magnetic field variations having a frequency higher than the first cutoff frequency, wherein each of the at least two feedback loops of the feedback circuit is configured to provide the rejected magnetic field variations for measurement as an output of the feedback circuit.

2. The magnetic field measurement system of claim 1, wherein the first cutoff frequency is in a range of 5 to 40 Hz.

3. The magnetic field measurement system of claim 1, wherein the first cutoff frequency is in a range of 8 to 20 Hz.

4. The magnetic field measurement system of claim 1, wherein each of the at least two feedback loops of the feedback circuit comprises a proportional integral derivative (PID) element.

5. The magnetic field measurement system of claim 4, wherein the first low pass filter is part of the PID element.

6. The magnetic field measurement system of claim 1, wherein the at least one magnetic field generator comprises two pairs of coils, wherein each of the pairs is arranged orthogonal to the other pair and is coupled to a different one of the at least two feedback loops.

7. The magnetic field measurement system of claim 1, wherein the feedback circuit comprises three of the feedback loops.

8. The magnetic field measurement system of claim 7, wherein the at least one magnetometer further comprises a pump light source configured to illuminate and pump atoms in the vapor cell.

9. The magnetic field measurement system of claim 7, wherein the at least one magnetic field generator comprises three pairs of coils, wherein each of the pairs is arranged orthogonal to the other pairs and is coupled to a different one of the three feedback loops.

10. The magnetic field measurement system of claim 7, wherein two of the three feedback loops of the feedback circuit further comprise a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit.

11. The magnetic field measurement system of claim 10, wherein two of the three feedback loops of the feedback circuit further comprise a modulation source configured to provide modulation at a modulation frequency to a feedback signal generated by the feedback circuit and delivered to the at least one magnetic field generator, wherein the modulation frequency is greater than the second cutoff frequency.

12. A magnetic field measurement system, comprising:
at least one magnetometer comprising a vapor cell, a light source configured to direct light through the vapor cell, and a detector configured to receive light directed through the vapor cell;
at least one magnetic field generator disposed adjacent the vapor cell and configured to modify a magnetic field experienced by the vapor cell; and
a feedback circuit coupled to the at least one magnetic field generator and the detector of the at least one magnetometer, wherein the feedback circuit comprises at least one feedback loop, wherein each of the at least one feedback loop comprises a first low pass filter with a first cutoff frequency, wherein the feedback circuit is configured to compensate for magnetic field variations having a frequency lower than the first cutoff frequency using the at least one magnetic field generator, wherein the first low pass filter rejects magnetic field variations having a frequency higher than the first cutoff frequency, wherein the feedback circuit is configured to provide the rejected magnetic field variations for measurement as an output of the feedback circuit, wherein at least one of the at least one feedback loop of the feedback circuit further comprises a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit.

13. The magnetic field measurement system of claim 12, wherein at least one of the at least one feedback loop of the feedback circuit further comprises a modulation source configured to provide modulation at a modulation frequency to a feedback signal generated by the feedback circuit and delivered to the at least one magnetic field generator, wherein the modulation frequency is greater than the second cutoff frequency.

14. The magnetic field measurement system of claim 12, wherein the feedback circuit comprises two of the feedback loops.

15. The magnetic field measurement system of claim 12, wherein the feedback circuit comprises three of the feedback loops.

16. A magnetic field measurement system, comprising:
an array of magnetometers, each of the magnetometers comprising a vapor cell, a light source configured to direct light through the vapor cell, and a detector configured to receive light directed through the vapor cell, wherein the array of magnetometers comprises a first magnetometer;
at least one magnetic field generator, wherein the vapor cell of each of the magnetometers is disposed adjacent at least one of the at least one magnetic field generator which is configured to modify a magnetic field experienced by the vapor cell; and
a feedback circuit coupled to each of the at least one magnetic field generator and the detector of the first magnetometer, wherein the feedback circuit comprises at least two feedback loops, wherein each of the at least two feedback loops comprises a first low pass filter with a first cutoff frequency, wherein each of the at least two feedback loops of the feedback circuit is configured to compensate, in each of the magnetometers, for magnetic field variations having a frequency lower than the first cutoff frequency using the at least one magnetic field generator, wherein the first low pass filter rejects magnetic field variations having a frequency higher than the first cutoff frequency, wherein the feedback circuit is configured to provide the rejected magnetic field variations for measurement as an output of the feedback circuit.

17. The magnetic field measurement system of claim 16, wherein each of the at least two feedback loops of the feedback circuit comprises a proportional integral derivative (PID) element.

18. The magnetic field measurement system of claim 17, wherein the first low pass filter is part of the PID element.

19. The magnetic field measurement system of claim 16, wherein at least one of the at least two feedback loops of the feedback circuit further comprises a second low pass filter having a second cutoff frequency, wherein the second cutoff frequency is higher than the first cutoff frequency, wherein the feedback circuit is configured to provide magnetic field variations having a frequency between the first cutoff frequency and the second cutoff frequency as the output of the feedback circuit.

20. The magnetic field measurement system of claim 16, wherein the feedback circuit comprises three of the feedback loops.

* * * * *